United States Patent [19]
Yoo

[11] Patent Number: 5,224,397
[45] Date of Patent: Jul. 6, 1993

[54] FINGER PRESSURE APPARATUS FOR A STEERING WHEEL COVER

[76] Inventor: Tae Woo Yoo, 807, 1-Dong, Hanyang Apt., San 189-1, Seocho-dong, Seocho-ku, Seoul, Rep. of Korea

[21] Appl. No.: 974,678

[22] Filed: Nov. 12, 1992

Related U.S. Application Data

[63] Continuation of Ser. No. 735,657, Jul. 25, 1991, abandoned.

[30] Foreign Application Priority Data

Sep. 25, 1990 [KR] Rep. of Korea ............... 14773

[51] Int. Cl.⁵ ................................. B62D 1/06
[52] U.S. Cl. ........................ 74/558; 74/552; 74/558.5
[58] Field of Search .......... 74/552, 558, 558.5

[56] References Cited

U.S. PATENT DOCUMENTS

| | | | |
|---|---|---|---|
| 1,446,628 | 2/1923 | Ridge | 74/558 |
| 3,468,188 | 9/1969 | MacCoon | 74/558 |

FOREIGN PATENT DOCUMENTS

| | | | |
|---|---|---|---|
| 1580112 | 7/1970 | Fed. Rep. of Germany | 74/558 |
| 1089449 | 3/1955 | France | 74/558 |
| 330243 | 6/1930 | United Kingdom | 74/558 |

Primary Examiner—Allan D. Herrmann
Assistant Examiner—William O. Trousdell
Attorney, Agent, or Firm—Felfe & Lynch

[57] ABSTRACT

A finger pressure apparatus for a steering wheel cover which has numerous projections for transferring negative ions from metallic elements constituting the apparatus to blood vessels upon the palms of the hands, thereby promoting blood circulation.

3 Claims, 1 Drawing Sheet

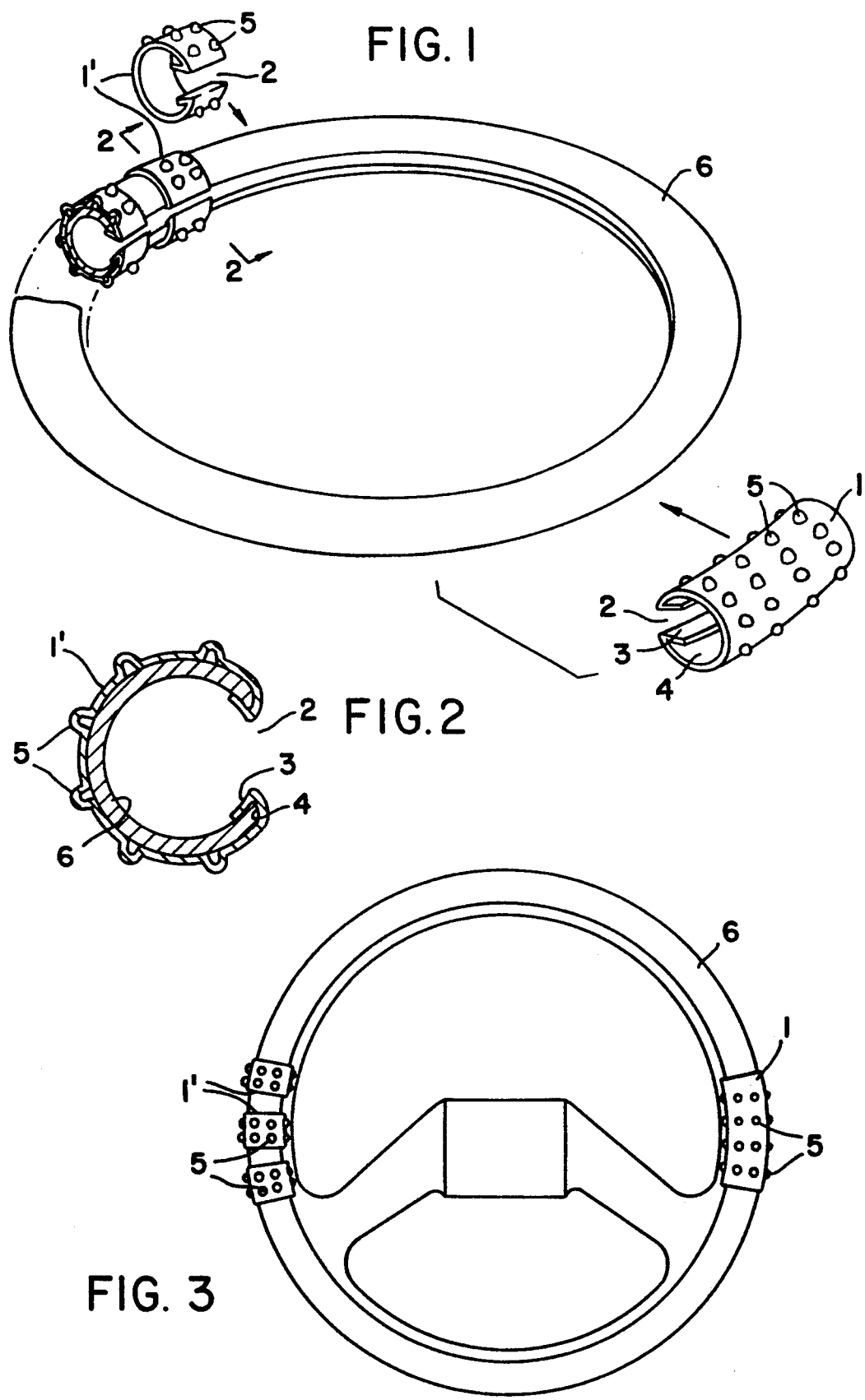

FINGER PRESSURE APPARATUS FOR A STEERING WHEEL COVER

This application is a continuation of application Ser. No. 735,657, filed Jul. 25, 1991 now abandoned.

This invention relates to a finger pressure apparatus for a cover for attachment to a steering wheel of various types of vehicles. More particularly, it relates to finger pressure apparatus for a steering wheel cover to which the apparatus made of metal ring portions with numerous projections is attached.

When the finger pressure apparatus is attached to various parts of a steering wheel cover, by virtue of the effect of finger pressure as well as the function of negative ions being produced from the metal portions, circulation of blood is accelerated.

With conventional steering wheels in most cases, the structure is made in such a way as to prevent slipping when grasped by the hands and to provide sturdy means to grasp. Hence its structure is usually rather simple; sometimes in the outer circumference of the steering wheel, projections could be found but they were not for the purpose of finger pressure but rather to improve the strength of friction at the time of grasping the steering wheel.

With this invention it is an object to avoid the defects being found with a conventional steering wheel cover. At the external surface of a metal approximately cylindrical body constituted with an open sectioned portion at one side, numerous projections are formed and the projections are attached preferably by insertion at a number of places at the exterior of a steering wheel cover. Hence, when the driver grasps the steering wheel, the driver comes to grip the external surface of the finger pressure apparatus attached to the cover of the steering wheel. Consequently, by means of numerous projections the effect of finger pressure can be gained simultaneously with the transfer of negative ions being produced either from aluminum or other metallic elements constituting the finger pressure apparatus to blood vessels upon the palms of the hands. By the provision of an ionization function, blood circulation is promoted.

In accordance with the invention, a finger pressure apparatus for a steering wheel cover comprises a sleeve-like ring-shaped body having an opening at one exterior side and having numerous projections extending outwardly from the circumference of the body, the body having an internally bent port portion forming a narrow groove.

For a better understanding of the invention, together with other and further objects thereof, reference is made to the following description, taken in connection with the accompanying drawings, and its scope will be pointed out in the appended claims.

Referring now to the drawings:

FIG. 1 is a fragmentary, perspective view of the finger pressure apparatus for application to a wheel cover;

FIG. 2 is a cross-sectional view taken along line 2—2 of FIG. 1, to an enlarged scale;

FIG. 3 is a plan view of the finger pressure apparatus on a wheel cover.

Referring now to FIGS. 1 and 2, a narrow line-like groove 4 is formed by cutting and bending the port portion 3 of sleeve-like ring-shaped approximately cylindrical body 1, 1' with an open section 2 being provided to one side of the external circumference. In the external circumference of cylindrical body 1, 1' numerous projections 5 formed by extrusion are then attached to the steering wheel cover 6 outwardly.

Regarding the functions and effects of this apparatus, with the structure mentioned above, the ring-shaped cylindrical body 1, 1' which is constituted of aluminum or alumnin plated metals or other metals with a high tendency for ionization. Because of an open portion 2 being formed as one side of the circumference, the internal surface is elastic and when a force within the limit of transformation according to the material's property is added, the internal surface has the property of tending to revert to the original state.

For this reason, when the cylindrical body 1, 1' is attached to a conventionally structured steering wheel cover 6 and when the internal radial portion is transformed in such a way as to distend the section 2 for insertion on the exterior of steering wheel cover 6 and when the force which was distending the open sectioned portion is removed, then by virtue of its own elasticity, the cylindrical body, 1, 1' returns to the original state and then the internal radial part of cylindrical body 1, 1' is tightly attached to the external portion of steering wheel cover 6.

At the same time the narrow groove 4 is formed by bending the port portion 3, the port portion of steering wheel cover 6 being inserted. Hence, a solid condition of attachment can be secured.

By virtue of the above mentioned functions, when the steering wheel cover with cylindrical body 1, 1' for finger pressure apparatus is attached to the steering wheel cover 6 and used on a steering wheel, it enables a firm grip on the steering wheel by heightening the strength of friction. At the same time with the tightened contact of the number of projections to the palms of hands and surfaces of the fingers, the effect of finger pressure is heightened. By means of ionic functions of metallic materials constituting the cylindrical body 1, 1' negative ions are transmitted to blood vessels upon the palm circulation of blood being promoted through the prevention of blood clotting and movement of negative ions and drastic reduction of positive ions which is a cause of pathogen of blood vessels.

While driving a car, the effect of finger pressure and improvement of blood circulation can be gained leading to removal of fatigue being accumulated through driving which will assist for assuring safety in driving.

While there has been described what is at present considered to be the preferred embodiment of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. A finger pressure apparatus for a steering wheel cover comprising:
    a sleeve-like ring-shaped body made of metal and having an opening at one exterior side and having numerous circumferentially spaced and laterally spaced projections extending outwardly from the circumference of said body said body having an internally bent port portion forming a narrow groove, said projections being effective to transmit negative ions to a palm of a drivers's hand upon tight end contact of a number of projections to the palm of the hand and to the driver's fingers.

2. Apparatus in accordance with claim 1 in which said metal is aluminum.

3. Apparatus in accordance with claim 1 in which said apparatus is aluminum-plated metal.

* * * * *